US00PP30505P2

(12) United States Plant Patent
Uchneat

(10) Patent No.: US PP30,505 P2
(45) Date of Patent: May 14, 2019

(54) ***HYPOESTES* PLANT NAMED 'G15180'**

(50) Latin Name: *Hypoestes phyllostachya*
Varietal Denomination: G15180

(71) Applicant: Michael S. Uchneat, Bellefonte, PA (US)

(72) Inventor: Michael S. Uchneat, Bellefonte, PA (US)

(73) Assignee: Garden Genetics LLC, Bellefonte, PA (US)

( * ) Notice: Subject to any disclaimer, the term of this patent is extended or adjusted under 35 U.S.C. 154(b) by 0 days.

(21) Appl. No.: 15/732,821

(22) Filed: Jan. 3, 2018

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. A. Whealy

(57) ABSTRACT

A new and distinct cultivar of *Hypoestes* plant named 'G15180', characterized by its upright and mounding plant habit; vigorous growth habit; freely branching habit; large dark green and white-colored leaves; and relative tolerance to high light conditions.

1 Drawing Sheet

Botanical designation: *Hypoestes phyllostachya*.
Cultivar denomination: 'G15180'.

BACKGROUND OF THE INVENTION

The present invention relates to a new and distinct cultivar of *Hypoestes* plant, botanically known as *Hypoestes phyllostachya* and hereinafter referred to by the name 'G15180'.

The new *Hypoestes* plant is a product of a planned breeding program conducted by the Inventor in Bellefonte, Pa. The objective of the breeding program is to create new vigorous *Hypoestes* plants with attractive leaves and high light tolerance.

The new *Hypoestes* plant originated from an open-pollination during the spring of 2015 in Bellefonte, Pa. of an unnamed proprietary seedling selection of *Hypoestes phyllostachya*, not patented, as the female, or seed, parent with an unknown proprietary seedling of *Hypoestes phyllostachya* as the male, or pollen, parent. The new *Hypoestes* plant was discovered and first selected by the Inventor as a single plant within the progeny of the stated open-pollination in a controlled greenhouse environment in Bellefonte, Pa. on Sep. 11, 2015.

Asexual reproduction of the new *Hypoestes* plant by terminal cuttings in a controlled greenhouse environment in Bellefonte, Pa. since Sep, 11, 2015 has shown that the unique features of this new *Hypoestes* plant are stable and reproduced true to type in successive generations.

SUMMARY OF THE INVENTION

Plants of the new *Hypoestes* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'G15180'.

These characteristics in combination distinguish 'G15180' as a new and distinct *Hypoestes* plant:

1. Upright and mounding plant habit.
2. Vigorous growth habit.
3. Freely branching habit.
4. Large dark green and white bi-colored leaves.
5. Relatively tolerant to high light conditions.

Compared to plants of the female parent selection, plants of the new *Hypoestes* differ primarily in the following characteristics:

1. Plants of the new *Hypoestes* are more vigorous than and not as compact as plants of the female parent selection.
2. Leaves of plants of the new *Hypoestes* are smoother than and not as crinkled as leaves of plants of the female parent selection.
3. Plants of the new *Hypoestes* are more tolerant to high light conditions than plants of the mutation parent selection.

Plants of the new *Hypoestes* can also be compared to plants of *Hypoestes phyllostachya* 'Splash Select White', not patented. In side-by-side comparisons, plants of the new *Hypoestes* differ primarily from plants of 'Splash Select White' in the following characteristics:

1. Plants of the new *Hypoestes* are more vigorous than and not as compact as plants of 'Splash Select White'.
2. Plants of the new *Hypoestes* have thicker leaves than plants of 'Splash Select White'.
3. Plants of the new *Hypoestes* are more tolerant to high light conditions than plants of 'Splash Select White'.

BRIEF DESCRIPTION OF THE PHOTOGRAPHS

The accompanying photographs illustrate the overall appearance of the new *Hypoestes* plant showing the colors as true as it is reasonably possible to obtain in colored reproductions of this type. Colors in the photographs may differ slightly from the color values cited in the detailed botanical description which accurately describe the colors of the new *Hypoestes* plant.

The photograph at the bottom of the sheet is a side perspective view of a typical plant of 'G15180' grown in a container.

The photograph at the top of the sheet is a close-up view of a typical plant of 'G15180'.

DETAILED BOTANICAL DESCRIPTION

The aforementioned photographs and following observations and measurements describe plants grown during the late summer and early autumn in 11.5 cm containers in an acrylic-covered greenhouse in Carleton, Mich. and under cultural practices typical of commercial potted *Hypoestes* production. During the production of the plants, day temperatures ranged from 18° C. to 28° C. and night temperatures ranged from 18° C. to 25° C. Plants were ten weeks old when the photographs and description were taken. In the following description, color references are made to The Royal Horticultural Society Colour Chart, 2007 Edition, except where general terms of ordinary dictionary significance are used.

Botanical classification: *Hypoestes phyllostachya* 'G15180'.

Parentage:

*Female, or seed, parent*.—Unnamed proprietary seedling selection of *Hypoestes phyllostachya*, not patented.

*Male, or pollen, parent*.—Unknown proprietary seedling of *Hypoestes phyllostachya*, not patented.

PROPAGATION:

*Type*.—By terminal cuttings.

*Time to initiate roots, summer*.—About 7 to 10 days at ambient temperatures about 22° C. to 27° C.

*Time to initiate roots, winter*.—About 10 to 14 days at ambient temperatures about 18° C. to 23° C.

*Time to produce a rooted plant, summer*.—About three to four weeks at ambient temperatures about 22° C. to 27° C.

*Time to produce a rooted plant, winter*.—About four weeks at temperatures about 18° C. to 23° C.

*Root description*.—Medium in thickness, fibrous; close to white in color, actual color of the roots is dependent on substrate composition, water quality, fertilizers, substrate temperature and age of roots.

*Rooting habit*.—Freely branching; medium density.

Plant description:

*Plant and growth habit*.—Upright and mounded plant form; freely branching habit with about three primary lateral branches each with about five to six secondary lateral branches developing per plant; vigorous growth habit and moderate growth rate.

*Plant height*.—About 12.5 cm.

*Plant diameter or spread*.—About 19 cm by 24 cm.

*Lateral branches*.—Length: About 9 cm. Diameter: About 2.5 mm. Internode length: About 2 cm. Strength: Strong. Aspect: Primary branches are mostly upright; secondary lateral branches are about 30° to 45° from vertical. Texture and luster, developing and developed: Minute pubescence; matte. Color: Developing and developed, close to 146A; at the nodes, close to 146B.

Leaf description:

*Arrangement*.—Opposite; simple.

*Length*.—About 7.7 cm.

*Width*.—About 5.8 cm.

*Shape*.—Broadly elliptical.

*Apex*.—Broadly acute.

*Base*.—Attenuate, equilateral.

*Margin*.—Entire.

*Venation pattern*.—Pinnate, arcuate.

*Texture and luster, upper and lower surfaces*.—Smooth, glabrous; matte.

*Color*.—Developing leaves, upper surface: Ground color, close to N137A; interveinal patches/splotches, close to 155A. Developing leaves, lower surface: Ground color, close to 147B; interveinal patches/splotches, close to 158C. Fully expanded leaves, upper surface: Ground color, slightly darker than 147A; interveinal patches/splotches, close to NN155C; venation, close to 147A. Fully expanded leaves, lower surface: Ground color, close to 147B to 147C and 148C; interveinal patches/splotches, close to 158C; venation, close to 146B.

*Petioles*.—Length: About 3.4 cm. Diameter: About 2 mm. Strength: Moderately strong. Texture and luster, upper and lower surfaces: Minute pubescence; matte. Color, upper and lower surfaces: Close to 146A.

Flower description: Flower initiation and development have not been observed on plants of the new *Hypoestes* to date.

Disease & pest resistance: Plants of the new *Hypoestes* have not been observed to be resistant to pathogens and pests common to *Hypoestes* plants to date.

Temperature tolerance: Plants of the new *Hypoestes* have been observed to tolerate low temperatures about 1.7° C. and to be suitable for USDA Hardiness Zones 10 and 11.

It is claimed:

1. A new and distinct *Hypoestes* plant named 'G15180' as illustrated and described.

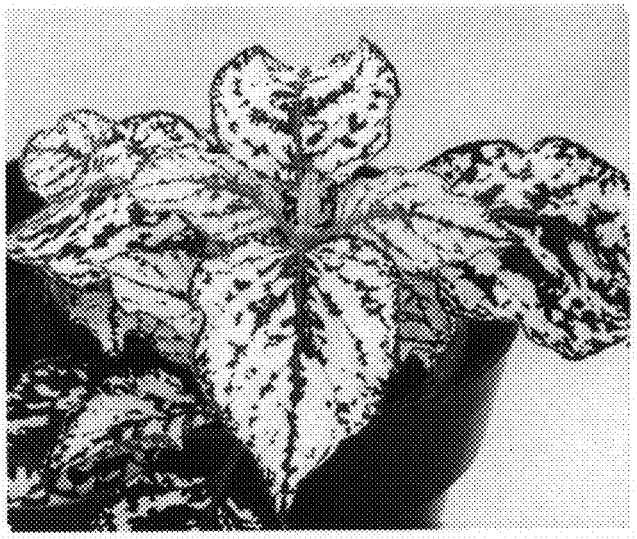
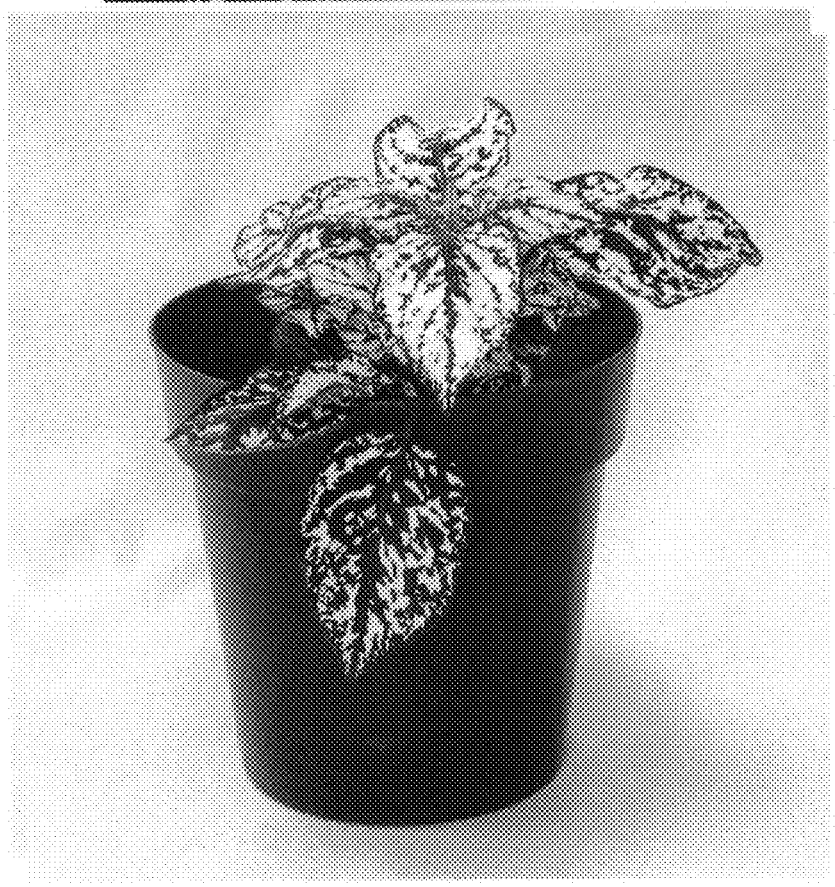

* * * * *